US00PP26471P2

(12) United States Plant Patent
Bernuetz et al.

(10) Patent No.: US PP26,471 P2
(45) Date of Patent: Mar. 8, 2016

(54) ***SCAEVOLA* PLANT NAMED 'BONSCA 1160'**

(50) Latin Name: *Scaevola aemula*
Varietal Denomination: BONSCA 1160

(71) Applicants: Andrew Bernuetz, Silverdale (AU); Mirza Mohammed Shoaib, North Parramata (AU)

(72) Inventors: Andrew Bernuetz, Silverdale (AU); Mirza Mohammed Shoaib, North Parramata (AU)

(73) Assignee: Bonza Botanicals PTY. LTD., Yellow Rock, NSW (AU)

( * ) Notice: Subject to any disclaimer, the term of this patent is extended or adjusted under 35 U.S.C. 154(b) by 177 days.

(21) Appl. No.: 13/999,241

(22) Filed: Jan. 31, 2014

(51) Int. Cl.
*A01H 5/02* (2006.01)

(52) U.S. Cl.
USPC ..... Plt./363

(58) Field of Classification Search
USPC ..... Plt./363
See application file for complete search history.

*Primary Examiner* — Anne Grunberg
(74) *Attorney, Agent, or Firm* — C. A. Whealy

(57) ABSTRACT

A new and distinct cultivar of *Scaevola* plant named 'BONSCA 1160', characterized by its compact, mounded and trailing plant habit; vigorous growth habit; freely branching habit; early and freely flowering habit; long flowering period; white-colored flowers; and good container and garden performance.

1 Drawing Sheet

Botanical designation: *Scaevola aemula.*
Cultivar denomination: 'BONSCA 1160'.

BACKGROUND OF THE INVENTION

The present invention relates to a new and distinct cultivar of *Scaevola* plant, botanically known as *Scaevola aemula* and hereinafter referred to by the name 'BONSCA 1160'.

The new *Scaevola* plant a product of a planned breeding program conducted by the Inventors in Yellow Rock, New South Wales, Australia. The objective of the breeding program is to create new compact, mounding, trailing and freely-flowering *Scaevola* plants with attractive flower color.

The new *Scaevola* plant originated from an open-pollination in Yellow Rock, New South Wales, Australia in October, 2009 of an unnamed proprietary selection of *Scaevola aemula,* not patented, as the female, or seed, parent with an unknown proprietary selection of *Scaevola aemula,* as the male, or pollen, parent. The new *Scaevola* plant was discovered and selected by the Inventors as a single flowering plant from within the progeny of the stated open-pollination in a controlled greenhouse environment in Yellow Rock, New South Wales, Australia on Mar. 15, 2011.

Asexual reproduction of the new *Scaevola* plant by vegetative cuttings in a controlled greenhouse environment in Yellow Rock, New South Wales, Australia since Mar. 15, 2011 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BONSCA 1160'. These characteristics in combination distinguish 'BONSCA 1160' as a new and distinct *Scaevola* plant:

1. Compact, mounded and trailing plant habit.
2. Vigorous growth habit.
3. Freely branching habit.
4. Early and freely flowering habit.
5. Long flowering period.
6. White-colored flowers.
7. Good container and garden performance.

Plants of the new *Scaevola* can be compared to plants of the female parent selection. Plants of the new *Scaevola* differ from plants of the female parent selection primarily in flower color.

Plants of the new *Scaevola* can be compared to plants of the *Scaevola aemula* 'Bonscawi', disclosed in U.S. Plant Pat. No. 19,520. In side-by-side comparisons, plants of the new *Scaevola* differed from plants of the 'Bonscawi' in the following characteristics:

1. Plants of the new *Scaevola* were smaller than plants of 'Bonscawi'.
2. Plants of the new *Scaevola* were not as upright as plants of 'Bonscawi'.
3 Plants of the new *Scaevola* had smaller leaves than plants of 'Bonscawi'.
4. Leaves of plants of the new *Scaevola* were narrowly spatulate in shape whereas leaves of plants of 'Bonscawi' were obovate in shape.
5. Plants of the new *Scaevola* were more freely flowering than plants of 'Bonscawi'.
6. Plants of the new *Scaevola* had larger flowers than plants of 'Bonscawi'.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'BONSCA 1160' grown in a container.

The photograph at the bottom of the sheet is a close-up view of a typical flowering plant of 'BONSCA 1160'.

DETAILED BOTANICAL DESCRIPTION

The aforementioned photographs and following observations, measurements and values describe plants grown in 20-cm containers during the summer in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Scaevola aemula* 'BONSCA 1160'.

Parentage:

*Female, or seed, parent*.—Unnamed proprietary selection of *Scaevola aemula,* not patented.

*Male or pollen parent*.—Unknown proprietary selection of *Scaevola aemula,* not patented.

Propagation:

*Type*.—By vegetative cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; white in color.

*Rooting habit*.—Freely branching; moderately dense.

Plant description:

*Plant form and growth habit*.—Compact, mounded and trailing plant habit; vigorous growth habit.

*Branching habit*.—Freely branching habit with lateral branches potentially forming at every node; pinching enhances branching potential.

*Plant height*.—About 11.3 cm.

*Plant diameter* (*area of spread*).—About 41.2 cm.

Lateral branch description:

*Length*.—About 23.3 cm.

*Diameter*.—About 2.2 mm.

*Internode length*.—About 2.35 cm.

*Aspect*.—Outwardly, decumbent.

*Texture*.—Pubescent.

*Color*.—Close to 143A.

Leaf description:

*Arrangement*.—Alternate, simple; sessile.

*Length*.—About 4.9 cm.

*Width*.—About 2.1 cm.

*Shape*.—Narrowly spatulate.

*Apex*.—Obtuse.

*Base*.—Cuneate.

*Margin*.—Serrate.

*Texture, upper and lower surfaces*.—Pubescent.

*Venation pattern*.—Pinnate, reticulate.

*Color*.—Developing leaves, upper surface: Close to 137A. Developing leaves, lower surface: Close to 137C. Fully expanded leaves, upper surface: Close to 137A; venation, close to 137A. Fully expanded leaves, lower surface: Close to 137D; venation, close to 137D.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from leaf axils; flowers face upright to outwardly; freely flowering habit with typically about 324 flowers developing per plant.

*Flowering time*.—Plants begin flowering after about four weeks after planting; long flower period, plants flower continuously from spring to late autumn in Japan.

*Flower longevity*.—Flowers typically last about a week on the plant; flowers persistent.

*Fragrance*.—None detected.

*Flower buds*.—Length: About 1.5 cm. Diameter: About 2.9 mm. Shape: Lenticular. Color: Close to 150C.

*Flowers*.—Diameter: About 1.6 cm by 2.8 cm. Tube length: About 1.3 cm. Tube diameter: About 3.6 mm.

*Petals*.—Quantity per flower: Five, fused at base. Length, above tube: About 1.5 cm. Width, above tube: About 5.1 mm. Shape: Narrowly elliptic. Apex: Cuspidate. Margin: Entire. Texture, upper and lower surfaces: Smooth, glabrous. Color: When opening, upper surface: Close to NN155C; longitudinal central stripe, close to 155B. When opening, lower surface: Close to NN155C; longitudinal central stripe, close to 145C. Fully opened, upper surface: Close to NN155C; longitudinal central stripe, close to 155B. Fully opened, lower surface: Close to NN155C; longitudinal central stripe, close to 145D. Throat: Close to N144A and 151C. Tube: Close to 151D.

*Sepals*.—Quantity per flower: Two. Length: About 5.7 mm. Width: About 1.5 mm. Shape: Lanceolate. Apex: Acute. Base: Decurrent. Margin: Entire. Texture, upper and lower surfaces: Slightly pubescent. Color: When developing, upper and lower surface: Close to 143C. Fully opened, upper surface: Close to 137B. Fully opened, lower surface: Close to 137D.

*Reproductive organs*.—Androecium: Stamen quantity per flower: Five. Anther shape: Ellipsoidal. Anther size: About 1.6 mm by 1 mm. Anther color: Close to 166A. Pollen: Scarce. Gynoecium: Pistil quantity per flower: One. Pistil length: About 1.2 cm. Style color: Close to 145C. Stigma shape: Narrowly oblong. Stigma color: Close to 145C. Ovary color: Close to 144A.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen & pest resistance: Plants of the new *Scaevola* have not been shown to be resistant to pathogens and pests common to *Scaevola* plants.

It is claimed:

1. A new and distinct *Scaevola* plant named 'BONSCA 1160' as illustrated and described.

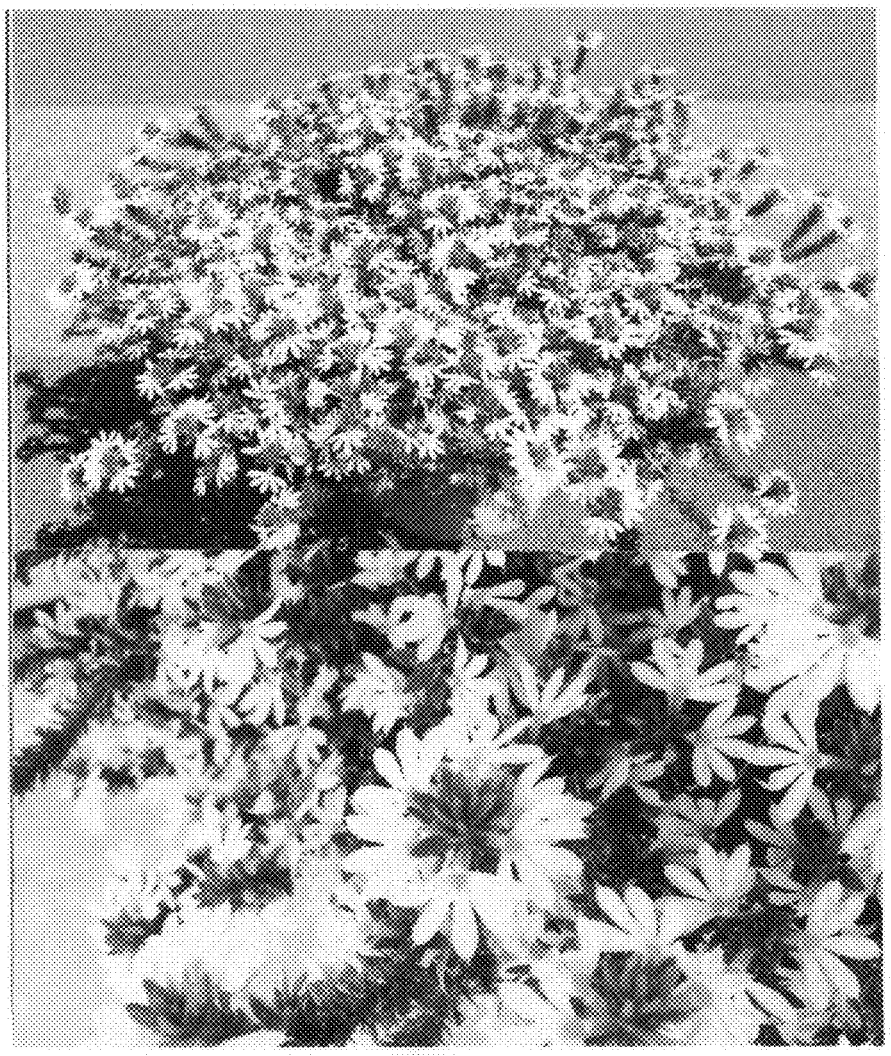

* * * * *